United States Patent
Jachmann et al.

(10) Patent No.: US 10,422,842 B2
(45) Date of Patent: Sep. 24, 2019

(54) NUCLEAR MAGNETIC RESONANCE $T_2$ RECOVERY PULSE

(71) Applicant: Halliburton Energy Services, Inc., Houston, TX (US)

(72) Inventors: Rebecca Corina Jachmann, Kingwood, TX (US); Jie Yang, Paoli, PA (US); Christopher Jon Conrad, Glen Mills, PA (US)

(73) Assignee: Halliburton Energy Services, Inc., Houston, TX (US)

( * ) Notice: Subject to any disclaimer, the term of this patent is extended or adjusted under 35 U.S.C. 154(b) by 389 days.

(21) Appl. No.: 14/432,441

(22) PCT Filed: Dec. 14, 2012

(86) PCT No.: PCT/US2012/069678
§ 371 (c)(1),
(2) Date: Mar. 30, 2015

(87) PCT Pub. No.: WO2014/092719
PCT Pub. Date: Jun. 19, 2014

(65) Prior Publication Data
US 2015/0293195 A1    Oct. 15, 2015

(51) Int. Cl.
*G01R 33/50* (2006.01)
*G01N 24/08* (2006.01)
(Continued)

(52) U.S. Cl.
CPC .......... *G01R 33/50* (2013.01); *G01N 24/081* (2013.01); *G01R 33/448* (2013.01);
(Continued)

(58) Field of Classification Search
CPC ............ G01R 33/44–586; G01V 3/32; G01N 24/08–088
(Continued)

(56) References Cited

U.S. PATENT DOCUMENTS 5,977,768 A * 11/1999 Sezginer ............. G01V 3/32
                                                        324/303
6,111,409 A *  8/2000 Edwards ............ G01N 24/081
                                                        324/303
(Continued)

FOREIGN PATENT DOCUMENTS

WO    WO-2014092719 A1    6/2014

OTHER PUBLICATIONS

"International Application Serial No. PCT/US2012/069678, International Search Report dated Sep. 11, 2013", 4 pgs.
(Continued)

*Primary Examiner* — Melissa J Koval
*Assistant Examiner* — Rahul Maini
(74) *Attorney, Agent, or Firm* — Haynes and Boone, LLP

(57) ABSTRACT

Various embodiments include apparatus and methods to conduct measurements on a structure using a nuclear magnetic resonance tool. The nuclear magnetic resonance tool can be operated to make nuclear magnetic resonance measurements that generate transverse 5 relaxation time echo train sequences ending with a recovery pulse. Additional apparatus, systems, and methods are disclosed.

27 Claims, 8 Drawing Sheets

(51) Int. Cl.
  *G01R 33/44* (2006.01)
  *G01R 33/54* (2006.01)
  *G01V 3/32* (2006.01)
  *G01R 33/561* (2006.01)

(52) U.S. Cl.
  CPC ............ *G01R 33/543* (2013.01); *G01V 3/32* (2013.01); *G01R 33/5617* (2013.01)

(58) Field of Classification Search
  USPC .................................................. 324/300–322
  See application file for complete search history.

(56) References Cited

U.S. PATENT DOCUMENTS

| | | | |
|---|---|---|---|
| 6,185,444 B1 * | 2/2001 | Ackerman | G01N 24/08 324/309 |
| 6,531,868 B2 * | 3/2003 | Prammer | G01N 24/081 324/303 |
| 6,690,167 B2 | 2/2004 | Reiderman et al. | |
| 6,717,404 B2 | 4/2004 | Prammer | |
| 7,196,516 B2 | 3/2007 | Blanz et al. | |
| 2001/0043066 A1 | 11/2001 | Hawkes et al. | |
| 2002/0175682 A1 | 11/2002 | Chen et al. | |
| 2003/0001569 A1 | 1/2003 | Chen et al. | |
| 2005/0275401 A1 | 12/2005 | Blanz et al. | |
| 2006/0192554 A1 | 8/2006 | Blanz et al. | |
| 2007/0032956 A1 | 2/2007 | Blanz et al. | |
| 2012/0194186 A1 | 8/2012 | Rehwald et al. | |
| 2012/0286779 A1 | 11/2012 | Walsh et al. | |
| 2013/0234706 A1 * | 9/2013 | Mandal | G01N 24/081 324/303 |

OTHER PUBLICATIONS

"International Application Serial No. PCT/US2012/069678, Written Opinion dated Sep. 11, 2013", 7 pgs.

Mitchell, J., et al., "A rapid measurement of T1/T2T1/T2: The DECPMG sequence", Journal of Magnetic Resonance, 200(2), (Oct. 2009), 198-206.

Prammer, M. G, et al., "A New Multiband Generation of NMR Logging Tools", SPE Reservoir Evaluation & Engineering, SPE-69670-PA, (2001), 59-63.

* cited by examiner

NUCLEAR MAGNETIC RESONANCE $T_2$ RECOVERY PULSE

PRIORITY APPLICATIONS

This application is a U.S. National Stage Filing under 35 U.S.C. 371 from International Application No. PCT/US2012/069678, filed on 14 Dec. 2012 and published as WO 2014/092719 on 19 Jun. 2014, which application and publication are incorporated herein by reference in their entirety.

TECHNICAL FIELD

The present invention relates generally to apparatus and methods of making and evaluating measurements, in particular, related to nuclear magnetic resonance methods.

BACKGROUND

Nuclear magnetic resonance (NMR) is used as a tool in a number of different technology areas to investigate different types of medium. NMR can occur when the medium is subjected to a static magnetic field and to an oscillating magnetic field. When subjected to an applied static magnetic field, polarization of nuclear magnetic spins of the medium occurs based on spin number of the medium. Applying an electromagnetic field to the medium in the static magnetic field can perturb the polarization established by the static magnetic field. In typical measurements, the static magnetic field and the perturbing field are perpendicular to each other. Collected responses received from the medium related to the total magnetization of nuclear spins in the medium, in response to these applied fields, can be used to investigate properties of the medium, and may provide imaging of the medium.

Nuclear magnetic resonance measurements are created by the oscillation of excited nuclear magnetic spins in the transverse plane, that is, the direction perpendicular to the magnetic field. This oscillation eventually dies out and the equilibrium magnetization returns. The return process is referred to as longitudinal relaxation. The time constant, $T_1$, for nuclei to return to their equilibrium magnetization $M_o$ is called the longitudinal relaxation time or the spin lattice relaxation time. The magnetization dephasing, that is losing coherence, along the transverse plane is given the time constant $T_2$ and is called the spin-spin relaxation time. The loss of phase coherence can be caused by several factors including interactions between spins or magnetic gradients.

A widely used NMR measurement technique, referred to as CPMG (in view of its designers Carr, Purcell, Meiboom, and Gill), uses a sequence of radio frequency pulses to produce spin echoes and counteract dephasing of the magnetization in the medium investigated. In the CPMG sequence, an initial pulse, commonly a 90° pulse, can be applied to tip the polarization into a plane perpendicular to the static magnetic field. To counter dephasing due to magnetic inhomogeneities, another pulse, a recovery pulse, is applied to return to phase, which produces a signal called an echo from the medium. Yet, after each return to phase, dephasing begins and another recovery pulse is applied for rephasing. Rephasing or refocusing is repeated many times in the CPMG sequence, while measuring each echo. The echo magnitude decreases with time due to a number of irreversible relaxation mechanisms. The CPMG sequence can have any number of echoes, where the time between each echo can be relatively short, for example, of the order of 1 ms or less or as long as 12 ms is used.

FIG. 1 illustrates use of a 90° tipping pulse and a sequence of 180° refocusing pulses. In this sequence, the ten 180° refocusing pulses cause ten echoes, where the peak amplitudes of the echoes are equally spaced apart by a peak to peak time distance, TE, that corresponds to the equally spaced apart time distances of the refocusing pulses. Also indicated is an acquisition window for capturing the signal of an echo. The echoes decay due to dephasing according to $T_2$ for the medium. Once the nuclear spin population is fully recovered for the sequence, the medium can be probed again by another sequence.

Petrophysical information can be derived from NMR measurements, such as, but not limited to petrophysical properties of fluid containing porous media. Various properties that can be measured using an NMR tool include pore size, porosity, surface-to-volume ratio, formation permeability, and capillary pressure. For instance, the distribution of $T_2$ values can be used to estimate pore size. As noted above, $T_2$ is related to loss of phase coherence that occurs among spins, which can be caused by several factors. For example, magnetic field gradients in pores lead to different decay rates. Thereby different pore sizes in the formation produce a distribution of $T_2$ values, which is shown in the conversion of spin-echo decay data of NMR measurements. This distribution represents a "most likely" distribution of $T_2$ values that produce the echo train of the measurement. This distribution can be correlated with a pore size distribution when the rock is 100% water saturated. However, if hydrocarbons are present, the $T_2$ distribution will be altered depending on the hydrocarbon type, viscosity, and saturation. With proper calibration and account for hydrogen index of the fluids in the pore space, the area under a $T_2$ distribution curve is equal to total porosity. More precision in the evaluation of NMR data may be aided with increased acquisition of data from multiple NMR measurements.

DETAILED DESCRIPTION

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

NMR logging tools have become a vital aspect in downhole logging. A limiting factor in NMR experiments is the necessity to wait for the magnetization to be fully polarized before repeating the measurement. The time allowed for magnetization to recover is known as a recovery time or wait time. This wait time limits the amount of data that can be collected from using a NMR tool downhole. $T_1$ experiments for collecting data related to $T_1$ have been constructed that reduce wait time limitations. Use of multi-band excitations (different frequencies) may greatly speed up the acquisition time of a set of data with different data collected at each frequency. However, there is still a long down time on each band to achieve full polarization. The needed repolarization time is commonly considered to be three to five times the longest $T_1$ component. Since longitudinal relaxation times underground can approach 3 to 5 seconds, common wait times are either 12 or 18 seconds.

In an embodiment, a recovery pulse is added at the end of a $T_2$ echo train sequence to recover any coherent magnetization. Coherent magnetization occurs when the nuclear spins are aligned. This allows the recovery process to begin with a magnetization of a medium at a level closer to its equilibrium magnetism than allowing to the medium to thermodynamically return to its equilibrium magnetism. Such a recovery pulse process can include generating a tipping pulse to start the sequence followed by a number, n, of refocusing pulses and a recovery pulse after the last of the refocusing pulses of the sequence. The recovery pulse can be applied at the time that corresponds to the maximum amplitude of the echo that would follow the last refocusing pulse of the sequence. The recovery pulse can be applied having the same orientation as the tipping pulse.

Figure 1:
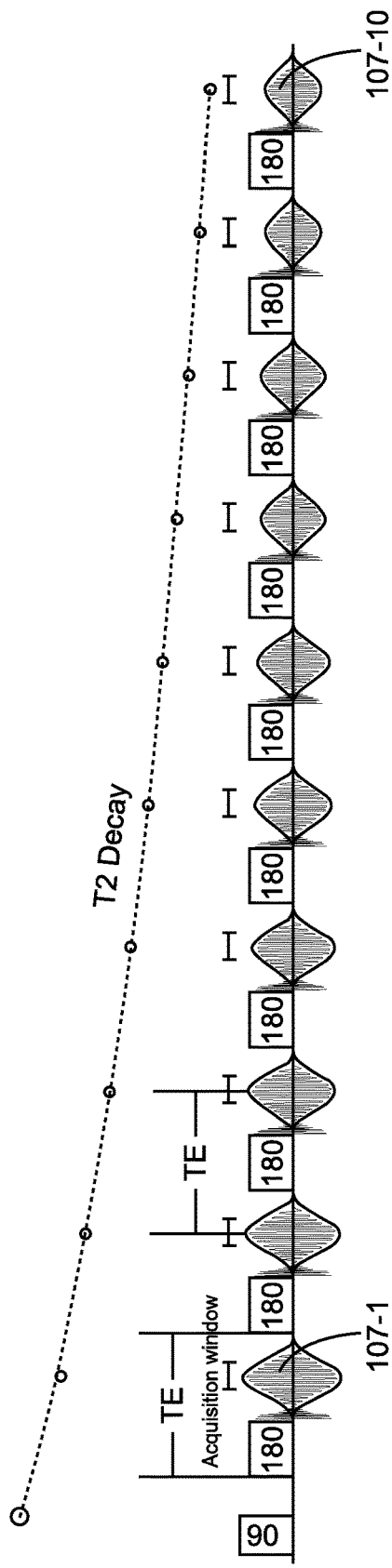
FIG. 1 illustrates use of a 90° tipping pulse and a sequence of 180° refocusing pulses, in accordance with various embodiments.
Figure 2:
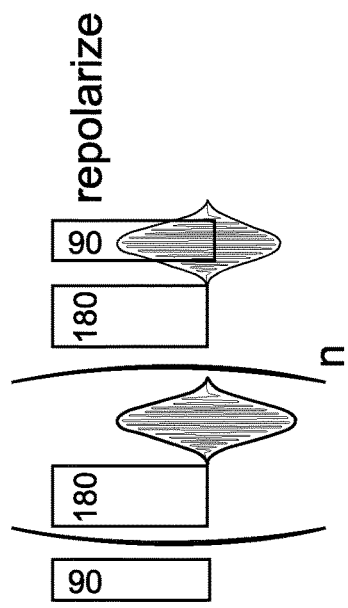
FIG. 2 illustrates a 90 degree tipping pulse, a sequence of a number, n, of 180 degree refocusing pulses, an end refocusing 180 degree pulse, and a 90 degree recovery pulse added at the end of the sequence, in accordance with various embodiments.

As depicted in FIG. 2, the tipping pulse can be a 90 degree pulse, the refocusing pulses can be 180 degrees pulses in a sequence of n refocusing pulses that are followed by echoes, an end refocusing 180 degree pulse, and the recovery pulse can be a 90 degree pulse added at the end of the $T_2$ echo train sequence. As shown, the recovery pulse can be applied at the time corresponding to the maximum amplitude of the echo that would follow the last refocusing pulse of the sequence. This addition recovery pulse, when utilized as a 90 degree pulse under certain conditions, can nearly double the data density acquired using multiple sequences. Each of these multiple sequences is applied after a waiting time corresponding to application of the recovery pulse. The tipping pulse, the refocusing pulses, and the recovery pulse are not limited to a 90° pulse, 180° pulses, and a 90° pulse, respectively. For example, a 45° tipping pulse, 135° refocusing pulses, and a 45° recovery pulse can be used to reduce the wait between sequences by providing a recovery starting point that is closer to the equilibrium magnetism than in a CPMG sequence having the same number of refocusing pulses.

The wait time needed after a recovery pulse can be evaluated with respect to the amount of magnetism that remains at the end of the echo train. The amount of magnetization left at the end of a 180° echo train is given by the signal, at time t:

$$\text{Signal} = \sum_{i}^{n} M_0 e^{-t/T_{2i} + D(\gamma G TE)^2 t/12},$$

where $M_0$ is the equilibrium magnetism, D is the fluid diffusivity, $\gamma$ is the gyromagnetic ratio, G is the magnetic field gradient, and TE is the time spacing between echoes in an echo train. The basic form of recovery, where the magnetism at time t is related to the equilibrium magnetism via $T_1$, is given by the relationship:

$$M(t) = M_0(1 - e^{-t/T_1}).$$

The starting point for recovery is related to how much time has been saved by using the recovery pulse, which can be calculated as:

$$T_{saved} = -T_1 \log(1 - \text{Signal}_{last\ echo}/M_0).$$

Similarly, the total time for recovery can be calculated as:

$$T_{Full\ Recovery} = -T_1 \log(1 - \text{SignalPercent}/M_0)$$

The recovery time using the recovery pulse is the difference between these two terms given by $$T_{Full\ Recovery} - T_{saved}.$$

Figure 3:
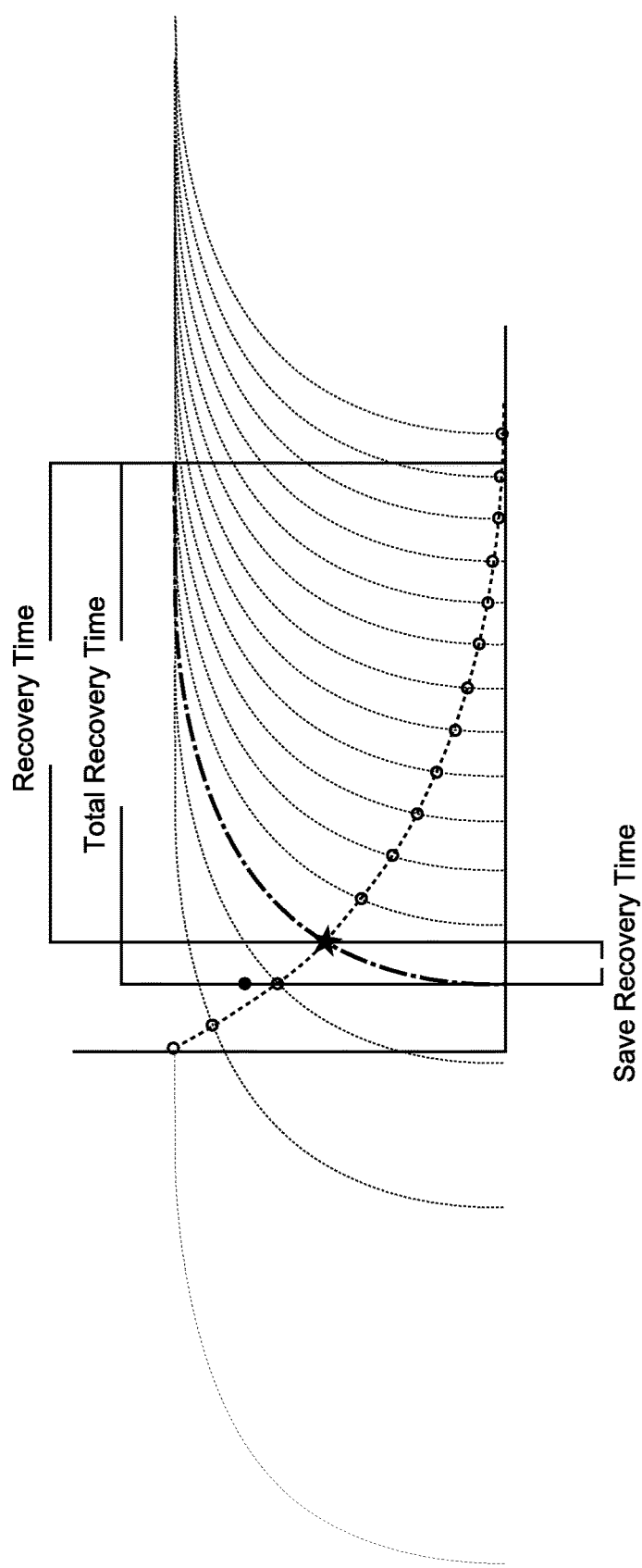
FIG. 3 depicts the relationship of the recovery time following a recovery pulse with respect to total recovery time and saved recovery time provided by the recovery pulse, in accordance with various embodiments.

The total recovery time is assigned a percent of signal recovered, since true full recovery is infinitely long. Thus, Signal Percent is the assigned percentage of the equilibrium magnetism. In terms of a porosity unit (pu), since only 1 pu accuracy is expected in a 30 pu formation, 97% recovery is considered efficient. Further, with calibration in this manner, there should be minimal error due to only getting 97% recovery. FIG. 3 depicts the relationship of the recovery time following a recovery pulse with respect to total recovery time and saved recovery time provided by the recovery pulse.

Figure 4:
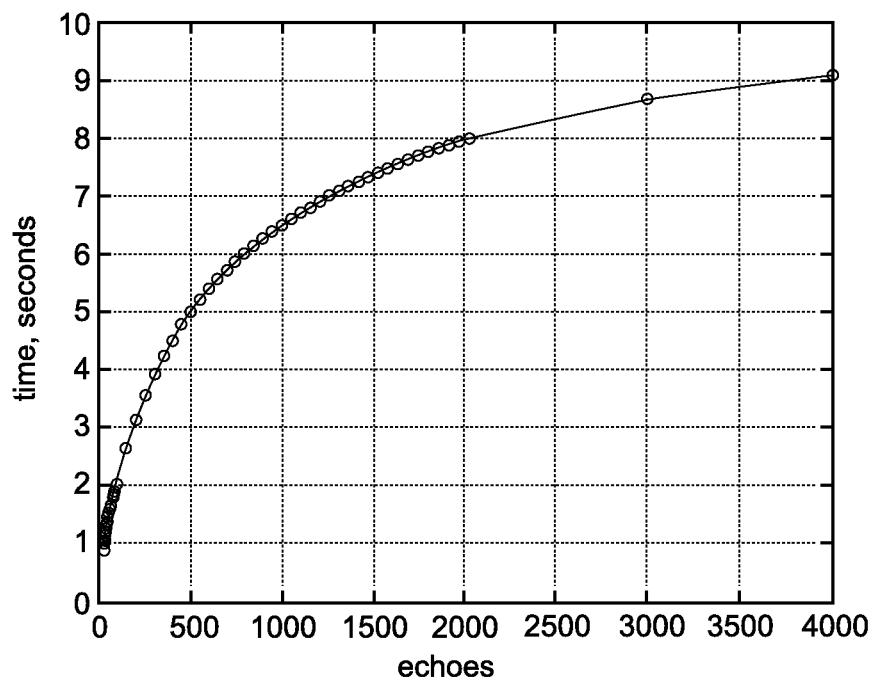
FIG. 4 shows wait times following a recovery pulse with respect to longitudinal relaxation time for an example sequence, in accordance with various embodiments.

FIG. 4 shows wait times following a recovery pulse with respect to longitudinal relaxation time for an example sequence. In this example, formations with a $T_1$ equal to 3 seconds are considered. The simulated NMR measurement is for a TE=0.6 ms and G=5 G/cm and a 97% recovery. As shown, after 1000 echoes, a wait time of just over 6.5 seconds is to be used after a recovery pulse of each sequence prior to generating the next sequence. Compared with the commonly used 12 to 18 seconds wait time without a recovery pulse, a time saving of about a factor of 2 to 3 can be obtained.

Figure 5:
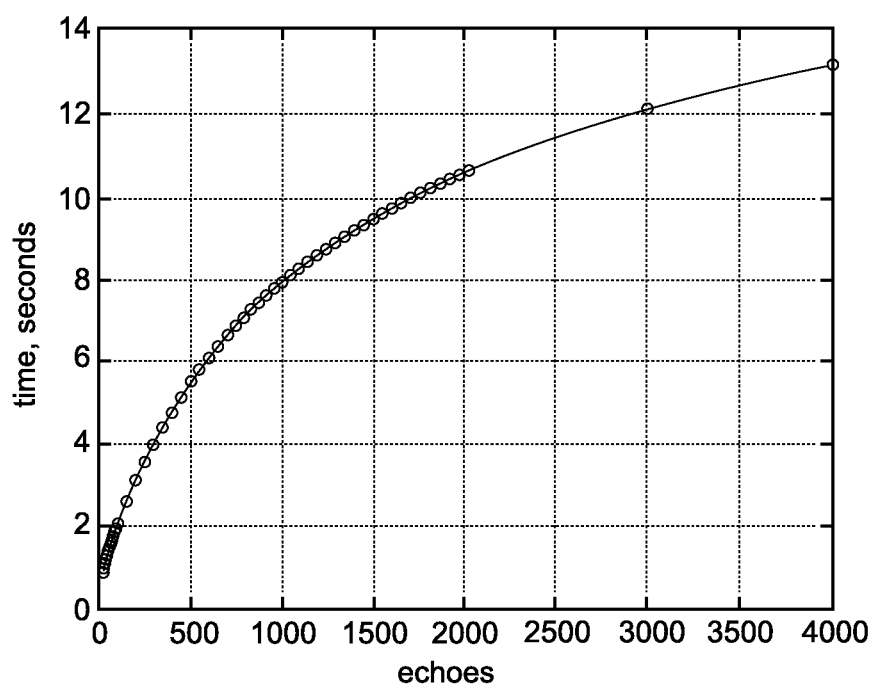
FIG. 5 shows recovery times following a recovery pulse with respect to longitudinal relaxation time for an example sequence, in accordance with various embodiments.

FIG. 5 shows recovery times following a recovery pulse with respect to longitudinal relaxation time for an example sequence. In this example, formations with long $T_1$s on the order of 5 seconds are considered. The simulated NMR measurement is for a TE=0.6 ms and G=5 G/cm. As shown, the 1000 echo experiment only needs about one more second of wait time to achieve 97% recovery than that shown in FIG. 4.

Figure 6:
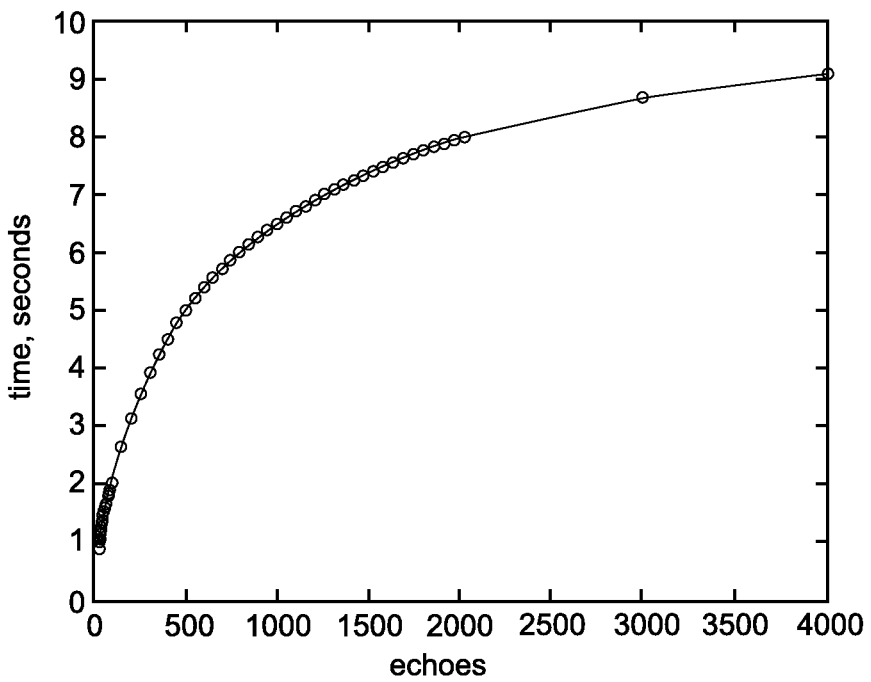
FIGS. 6-9 shows calculations for recovery times following a recovery pulse for different combinations of magnetic gradient and longitudinal relaxation time, in accordance with various embodiments.
Figure 7:
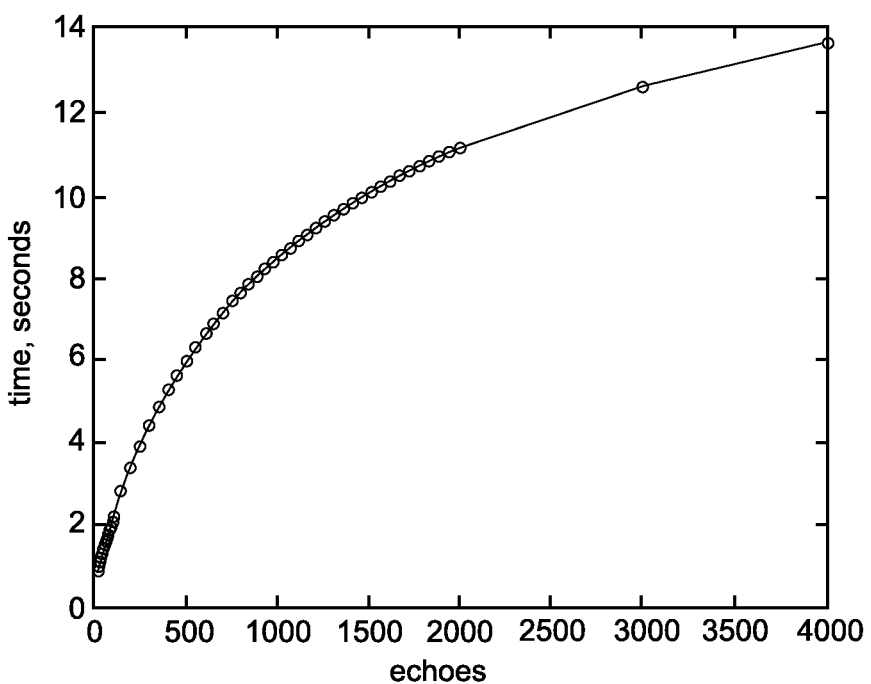
Figure 8:
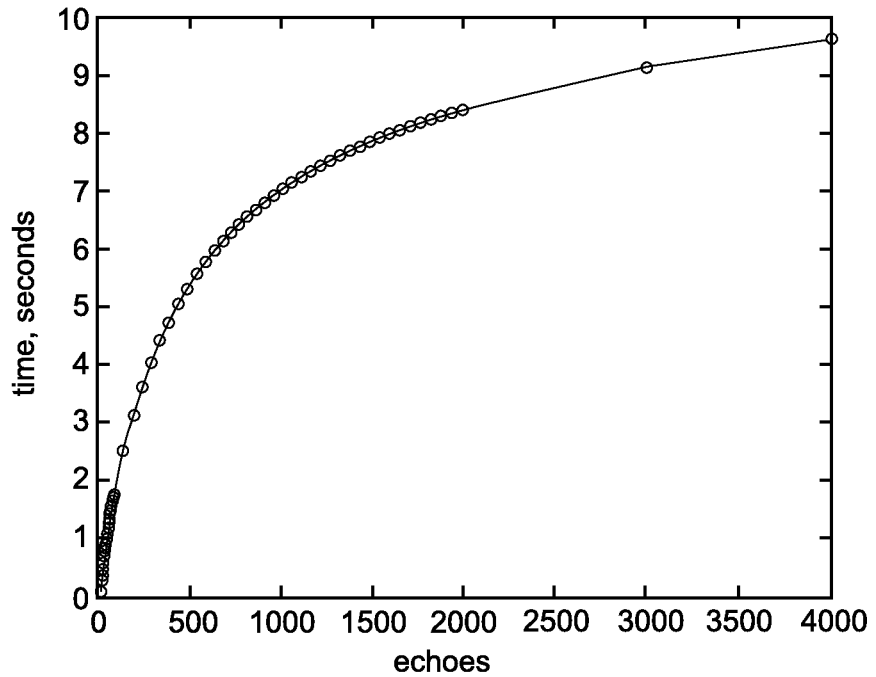
Figure 9:
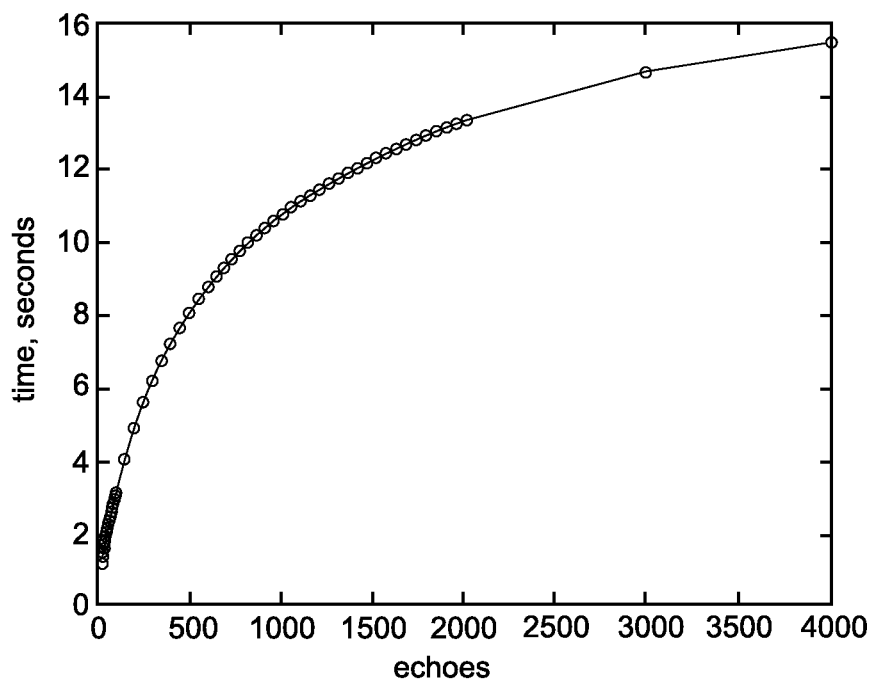

A system using a recovery pulse may work best in low gradients with short TE sequences, since diffusion does not affect the loss in magnetization as much in these conditions. In higher gradients, the effectiveness of this technique will diminish. FIGS. 6-9 shows recovery times following a recovery pulse for different combinations of magnetic gradient and longitudinal relaxation time. FIG. 6 shows recovery times for TE=0.6 ms, G=9 G/cm, $T_1$=3. FIG. 7 shows recovery times for TE=0.6 ms, G=9 G/cm, $T_1$=5. FIG. 8 shows recovery times for TE=0.6 ms, G=22 G/cm, $T_1$=3. FIG. 9 shows recovery times for TE=0.6 ms, G=22 G/cm, $T_1$=5.

Figure 10:
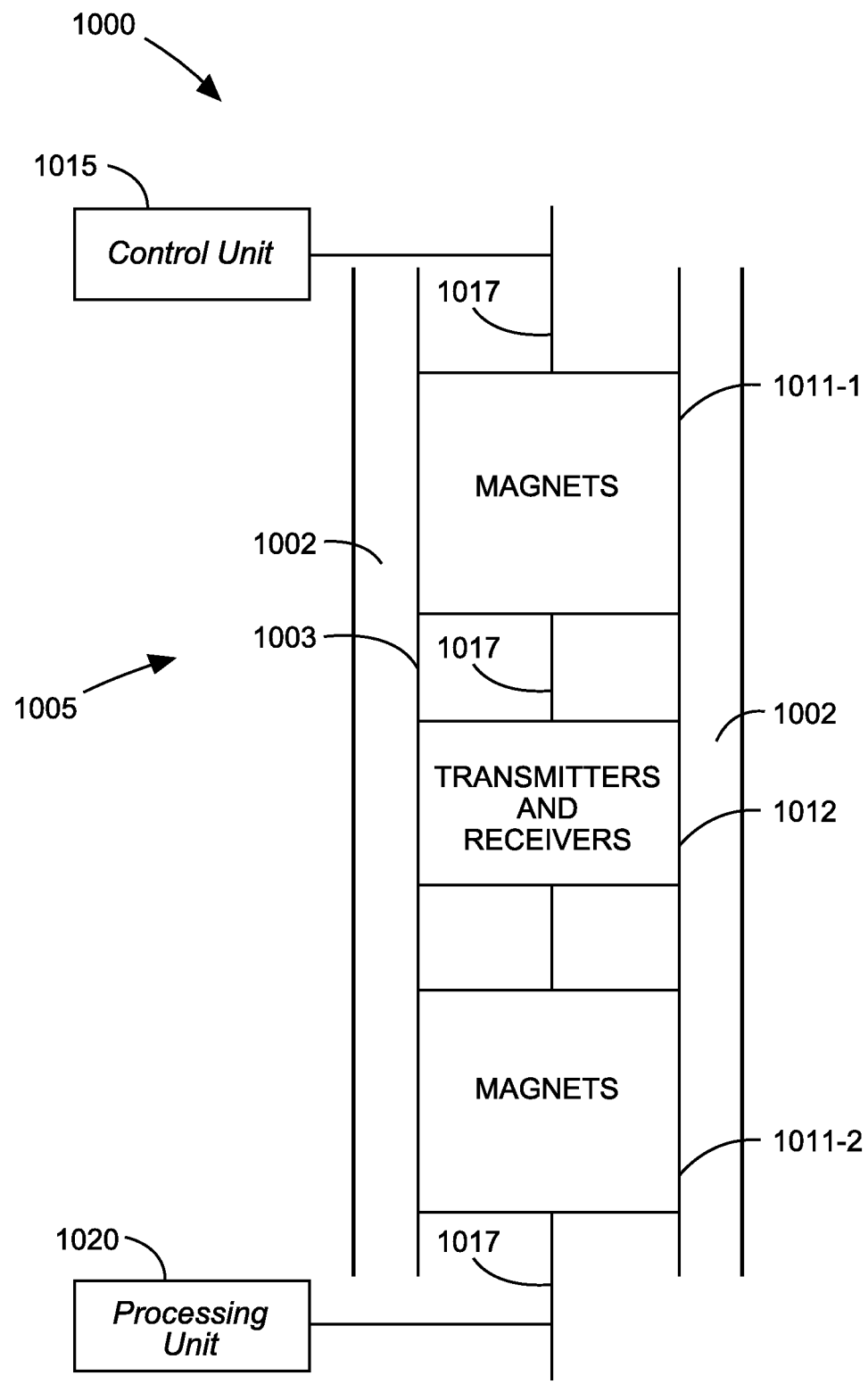
FIG. 10 depicts a block diagram of features of an example nuclear magnetic resonance tool operable in a borehole, in accordance with various embodiments.

FIG. 10 shows a block diagram of an example embodiment of a system 1000 structured to determine properties of a region of a borehole 1002 subject to nuclear magnetic resonance measurements. The system 1000 includes a nuclear magnetic resonance tool 1005 having a tool structure 1003, a control unit 1015, and a processing unit 1020. The tool structure 1003 has an arrangement of magnets 1011-1 and 1011-2 and transmitters and receivers 1012 under the control of control unit 1015. The transmitters and receivers 1012 can be realized as transceivers. These transmitters and receivers 1012 may be arranged with respect to a longitudinal axis 1017 of the tool structure 1003, though they need not be arranged relative to the longitudinal axis 1017. The control unit 1015 can be operable to manage generation and collection of signals from the one or more transmitters and receivers 1012. The generation of signals can include generating a number of $T_2$ echo train sequences. Each echo train sequence can include a tipping pulse, a sequence of n refocusing pulses, an end refocusing pulse, and a recovery pulse added following the end refocusing pulse. These pulses can include a 90 degree tipping pulse, 180 degree refocusing pulses, and a 90 degree recovery pulse. The control unit 1014 can selectively generate tipping, refocusing, and recovery pulses at other orientations. The processing unit 1020 of the system 1000 can be structured to process the received signals to determine properties of the region of the borehole 1002 investigated by the nuclear magnetic resonance tool 1005. The nuclear magnetic resonance tool 1005 can be structured with the processing unit 1020 and the control unit 1015 integrated with the tool structure 1003 or structured as distributed components. Distributed components can include components housed on the surface at a drilling location or downhole. In addition, the processing unit 1020 and the control unit 1015 can be realized as an integrated unit housed on the surface at a drilling location or downhole.

Figure 11:
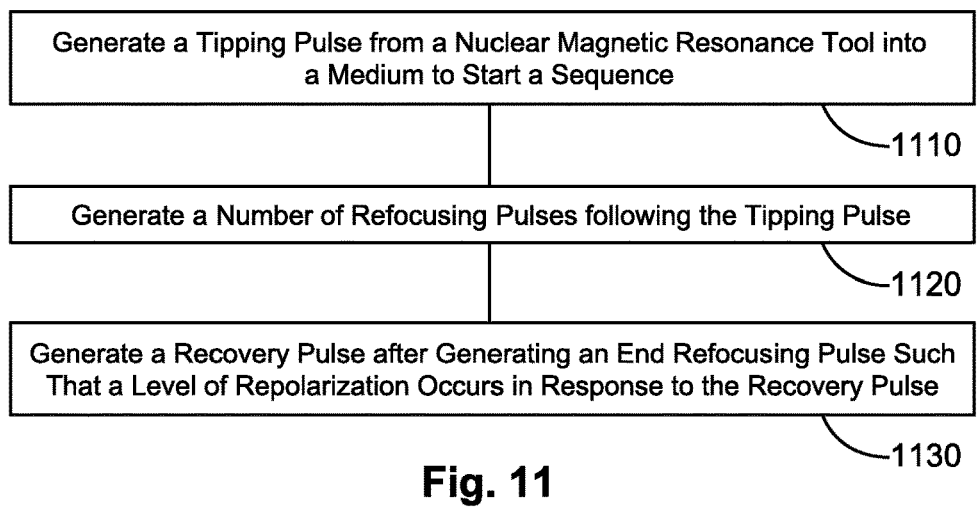
FIG. 11 shows features of an example method of conducting a nuclear magnetic resonance measurement including generating a recovery pulse to recover magnetism, in accordance with various embodiments.

FIG. 11 shows features of a method of conducting a NMR measurement including generating a recovery pulse to recover magnetism. At 1110, a tipping pulse from a nuclear magnetic resonance tool is generated into a medium. The tipping pulse starts a sequence, where the sequence is a $T_2$ echo train pulse sequence. In the $T_2$ echo train pulse sequence, the tipping pulse can be a 90° pulse. The tipping pulse can be a 45° pulse or a pulse with another flipping angle.

At 1120, a number of refocusing pulses are generated following the tipping pulse as part of the sequence. The $T_2$ echo train pulse sequence has an end refocusing pulse. In the $T_2$ echo train pulse sequence, the refocusing pulses can be 180° pulses. The refocusing pulses can be a 135° pulse or pulses with other flipping angles.

At 1130, a recovery pulse is generated after generating the end refocusing pulse such that a level of repolarization occurs in response to the recovery pulse. The recovery pulse can be applied at a center of an echo following the end refocusing pulse. The recovery pulse can be a 90° pulse. The recovery pulse can be a 45° pulse or a pulse with another flipping angle. The level of repolarization can be an effective total repolarization. The level of repolarization can be assigned as a percentage of full repolarization. The assigned percentage can be ninety-seven percent. Other percentages can be assigned.

In the $T_2$ echo train pulse sequence, the tipping pulse can be a 90° pulse, each refocusing pulse can be a 180° pulse, and the recovery pulse can be a 90° pulse. Sets of pulses can be generated with other flipping angles. The method of conducting the NMR measurement can include, after a wait time from generating the recovery pulse, generating another tipping pulse from the nuclear magnetic resonance tool into the medium to start another $T_2$ echo train pulse sequence. The wait time can be based on the number of refocusing pulses and the level of repolarization used in the sequence. The wait time can be 5 seconds or other time selected according to the particular measurement arrangement. The number of refocusing pulses used in a recovery pulse process can be selected such that the number of refocusing pulses corresponding to a wait time less than 12 seconds.

The method of conducting the NMR measurement can include generating a number of $T_2$ echo train pulse sequences, where each $T_2$ echo train pulse sequence is generated at a frequency different from the other $T_2$ echo train pulse sequences. For example, five frequencies can be used. In addition, during the wait time in one sequence, another sequence can be generated at a different frequency.

In operating the NMR tool in a borehole, the NMR tool can be pulled or pushed throughout the borehole taking measurements at different depths. Using the recovery pulse, the wait time can be shorter than 12 to 18 seconds as is customarily used in $T_2$ echo train measurements. With the lower wait time, more measurements can be taken and the amount of data collected in a given time of measurement can be increased (data density is increased). With increased measurements at different depths, enhanced vertical resolution may be obtained. The increased data can also provide for an increased signal-to-noise ratio.

In various embodiments, components of a system operable to conduct nuclear magnetic resonance measurements, as described herein or in a similar manner, can be realized in software, hardware, or combinations of hardware and software based implementations. These implementations can include a machine-readable storage device having machine-executable instructions, such as a computer-readable storage device having computer-executable instructions, to generate a tipping pulse from a nuclear magnetic resonance tool into a medium to start a sequence, the sequence being a transverse relaxation time ($T_2$) echo train pulse sequence; to generate a number of refocusing pulses following the tipping pulse as part of the sequence, the $T_2$ echo train pulse sequence having an end refocusing pulse; and to generate a recovery pulse after generating the end refocusing pulse such that a level of repolarization occurs in response to the recovery pulse. The tipping pulse can be a 90° pulse, each refocusing pulse can be a 180° pulse, and the recovery pulse can be a 90° pulse. The recovery pulse can be applied at a center of an echo following the end refocusing pulse. The level of repolarization can be assigned as a percentage of full repolarization. For example, the percentage can be ninety-seven percent.

The operations can include operations to, after a wait time from generating the recovery pulse, generate another tipping pulse from the nuclear magnetic resonance tool into the medium to start another $T_2$ echo train pulse sequence, the wait time being based on the number of refocusing pulses and the level of repolarization. The number of refocusing pulses can be based on a selected wait time. For example, the number of refocusing pulses is less than a number of refocusing pulses corresponding to a wait time of 5 seconds. The operations can include operations to generate a number of $T_2$ echo train pulse sequences, each $T_2$ echo train pulse sequence at a frequency different from the other $T_2$ echo train pulse sequences.

Executed instructions can also include instructions to operate a tool having one or more transmitters and one or more receivers of a nuclear magnetic resonance tool to generate tipping pulses, refocusing pulses, and recovery pulses in accordance with the teachings herein. The instructions can include instructions to provide data to a processing unit such that the processing unit conducts one or more processes to evaluate signals, data, or signals and data. Further, a machine-readable storage device, herein, is a physical device that stores data represented by physical structure within the device. Examples of machine-readable storage devices include, but are not limited to, read only memory (ROM), random access memory (RAM), a magnetic disk storage device, an optical storage device, a flash memory, and other electronic, magnetic, and/or optical memory devices.

In various embodiments, a system can comprise a nuclear magnetic resonance tool; and a control unit coupled to the nuclear magnetic resonance tool to control the nuclear magnetic resonance tool to perform operations to: generate a tipping pulse from a nuclear magnetic resonance tool into a medium to start a sequence, the sequence being a transverse relaxation time ($T_2$) echo train pulse sequence; generate a number of refocusing pulses following the tipping pulse as part of the sequence, the $T_2$ echo train pulse sequence having an end refocusing pulse; and generate a recovery pulse after generating the end refocusing pulse such that a level of repolarization occurs in response to the recovery pulse. The tipping pulse can be a 90° pulse, each refocusing pulse can be a 180° pulse, and the recovery pulse can be a 90° pulse. The recovery pulse can be applied at a center of an echo following the end refocusing pulse. The level of repolarization can be assigned as a percentage of full repolarization. For example, the percentage can be ninety-seven percent.

The system can be arranged to conduct operations that include operations to, after a wait time from generating the recovery pulse, generate another tipping pulse from the nuclear magnetic resonance tool into the medium to start another $T_2$ echo train pulse sequence, the wait time being based on the number of refocusing pulses and the level of repolarization. The number of refocusing pulses can be based on a selected wait time. For example, the number of refocusing pulses is less than a number of refocusing pulses corresponding to a wait time of 5 seconds. The system can be arranged to conduct operations that include operations to generate a number of $T_2$ echo train pulse sequences, each $T_2$ echo train pulse sequence at a frequency different from the other $T_2$ echo train pulse sequences.

Figure 12:
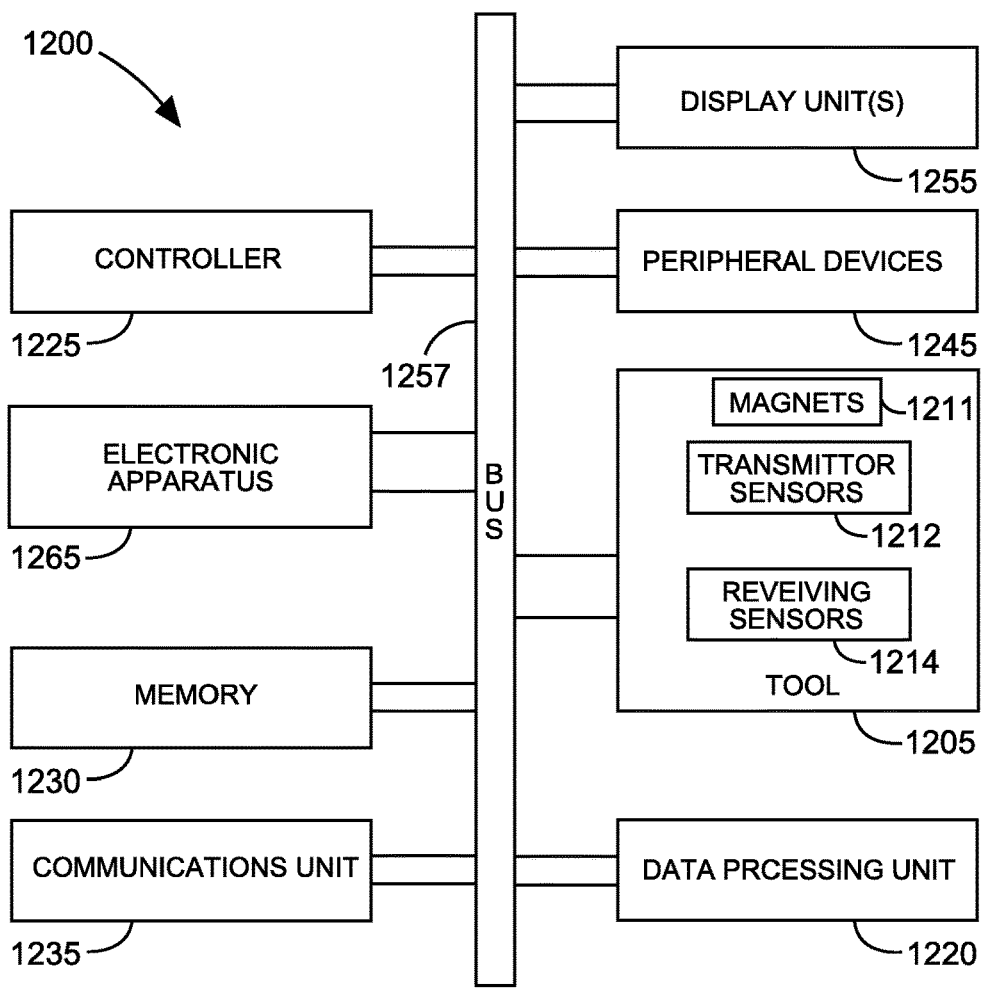
FIG. 12 depicts a block diagram of features of an example system having a nuclear magnetic resonance tool, in accordance with various embodiments.

FIG. 12 depicts a block diagram of features of an example embodiment of a system 1200 operable to make nuclear magnetic resonance measurements that generate $T_2$ echo train sequences ended with a recovery pulse, as described herein or in a similar manner. The system 1200 can include a tool 1205 having an arrangement of magnets 1211, transmitter sensors 1212, and receiver sensors 1214 that can be realized in a similar or identical manner to arrangements of sensors discussed herein. The system 1200 can be configured to operate in accordance with the teachings herein.

The system 1200 can include a controller 1225, a memory 1230, an electronic apparatus 1265, and a communications unit 1235. The memory 1230 can be structured to include a database. The controller 1225, the memory 1230, and the communications unit 1235 can be arranged to operate as a processing unit to control operation of the transmitters 1212 and the receivers 1214 and to perform operations on the signals collected by the receivers 1214 to conduct nuclear magnetic resonance inversion processes. A processing unit 1220, structured to conduct nuclear magnetic resonance inversion processes, can be implemented as a single unit or distributed among the components of the system 1200 including electronic apparatus 1265. The controller 1225 and the memory 1230 can operate to control activation of the transmitters 1212 to generate $T_2$ echo train sequences ended with a recovery pulse. The controller 1225 and the memory 1230 can operate to control selection of the receiver sensors in the tool 1205 and to manage processing schemes. The controller 1225, the memory 1230, and other components of the system 1200 can be configured, for example, to operate similar to or identical to the components discussed herein or similar to or identical to any of methods discussed herein.

The communications unit 1235 can include downhole communications for appropriately located sensors in a drilling operation. Such downhole communications can include a telemetry system. The communications unit 1235 may use combinations of wired communication technologies and wireless technologies at frequencies that do not interfere with on-going measurements.

The system 1200 can also include a bus 1227, where the bus 1227 provides electrical conductivity among the components of the system 1200. The bus 1227 can include an address bus, a data bus, and a control bus, each independently configured or in an integrated format. The bus 1227 can be realized using a number of different communication mediums that allows for the distribution of components of the system 1200. Use of the bus 1227 can be regulated by the controller 1225.

In various embodiments, the peripheral devices 1245 can include additional storage memory and other control devices that may operate in conjunction with the controller 1225 and the memory 1230. In an embodiment, the controller 1225 can be realized as a processor or a group of processors that may operate independently depending on an assigned function.

The system 1200 can include display unit(s) 1255 as a distributed component on the surface at a drilling operation, which can be used with instructions stored in the memory 1230 to implement a user interface to monitor the operation of the tool 1205 or components distributed within the system 1200. The user interface may be used to input parameter values for thresholds such that the system 1200 can operate autonomously substantially without user intervention. The user interface can also provide for manual override and change of control of the system 1200 to a user. Such a user interface can be operated in conjunction with the communications unit 1235 and the bus 1227.

Figure 13:
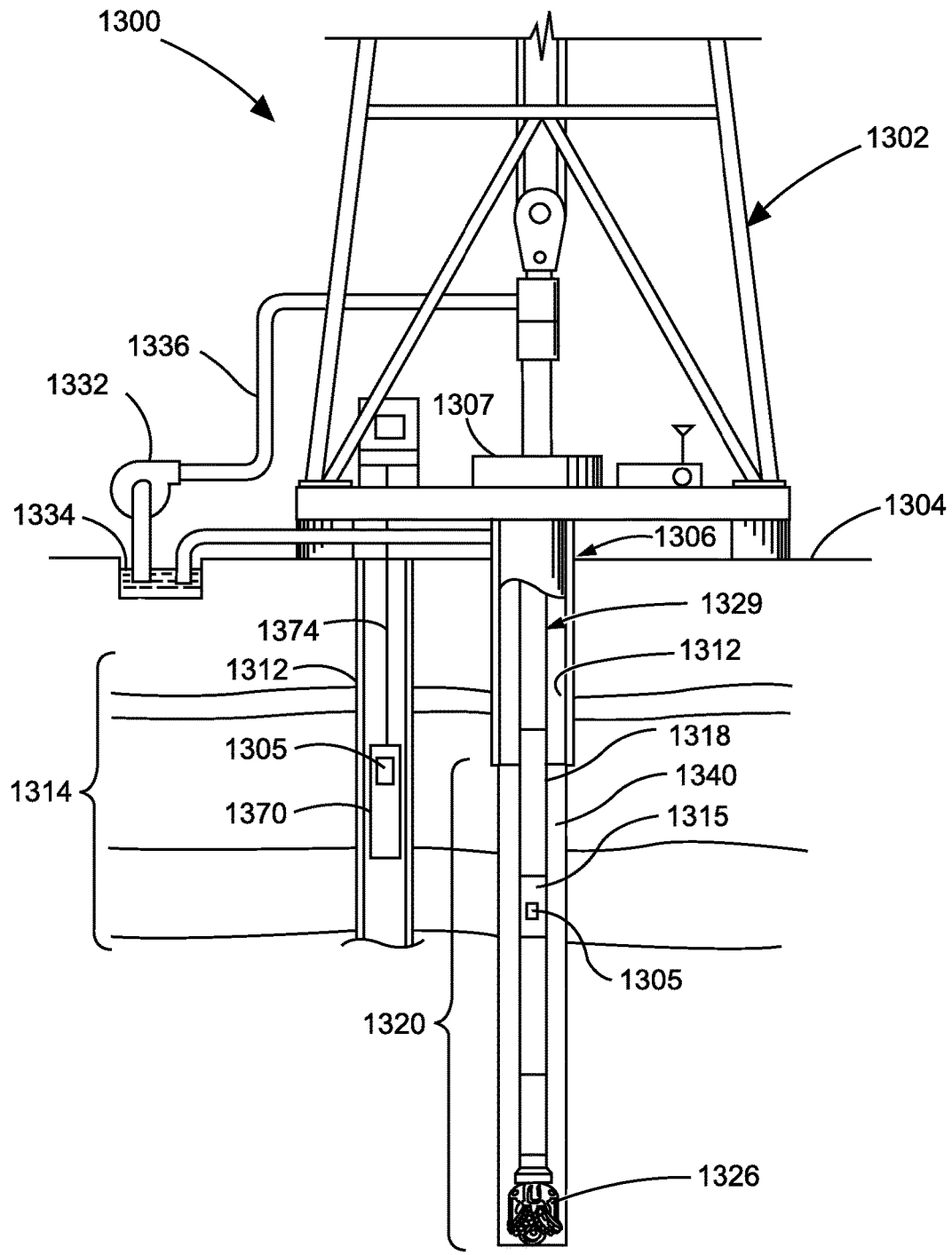
FIG. 13 depicts an example system at a drilling site, where the system includes a tool configured with a nuclear magnetic resonance tool, in accordance with various embodiments.

FIG. 13 depicts an embodiment of a system 1300 at a drilling site, where the system 1300 includes a tool 1305 having a control unit and a nuclear magnetic resonance tool operable to make nuclear magnetic resonance measurements that generate $T_2$ echo train sequences ending with a recovery pulse, as described herein or in a similar manner. The tool 1305 can be distributed among the components of system 1300. The tool 1305 can be realized in a similar or identical manner to arrangements of control units, transmitters, receivers, and processing units discussed herein. The tool 1305 can be structured and fabricated in accordance with various embodiments as taught herein with respect to transmitters, receivers, control units, and processing units to perform nuclear magnetic resonance measurements that generate $T_2$ echo train sequences ending with a recovery pulse.

The system 1300 can include a drilling rig 1302 located at a surface 1304 of a well 1306 and a string of drill pipes, that is, the drill string 1308, connected together so as to form a drilling string that is lowered through a rotary table 1307 into a wellbore or borehole 1312. The drilling rig 1302 can provide support for the drill string 1308. The drill string 1308 can operate to penetrate the rotary table 1307 for drilling the borehole 1312 through subsurface formations 1314. The drill string 1308 can include drill pipe 1318 and a bottom hole assembly 1320 located at the lower portion of the drill pipe 1318.

The bottom hole assembly 1320 can include a drill collar 1315, the tool 1305 attached to the drill collar 1315, and a drill bit 1326. The drill bit 1326 can operate to create the borehole 1312 by penetrating the surface 1304 and the subsurface formations 1314. The tool 1305 can be structured for an implementation in the borehole 1312 as a measurement while drilling (MWD) system such as a logging while drilling (LWD) system. The housing containing the tool 1305 can include electronics to activate one or more transmitters of the tool 1305 and collect responses from one or more receivers of the tool 1305. Such electronics can include a processing unit to conduct nuclear magnetic resonance inversion and provide results to the surface over a standard communication mechanism for operating a well. Alternatively, electronics can include a communications interface to provide signals output by receivers of the tool 1305 to the surface over a standard communication mechanism for operating a well, where these output signals can be analyzed at a processing unit at the surface to conduct nuclear magnetic resonance inversion.

During drilling operations, the drill string 1308 can be rotated by the rotary table 1307. In addition to, or alternatively, the bottom hole assembly 1320 can also be rotated by a motor (e.g., a mud motor) that is located downhole. The drill collars 1315 can be used to add weight to the drill bit 1326. The drill collars 1315 also can stiffen the bottom hole assembly 1320 to allow the bottom hole assembly 1320 to transfer the added weight to the drill bit 1326, and in turn, assist the drill bit 1326 in penetrating the surface 1304 and subsurface formations 1314.

During drilling operations, a mud pump 1332 can pump drilling fluid (sometimes known by those of skill in the art as "drilling mud") from a mud pit 1334 through a hose 1336 into the drill pipe 1318 and down to the drill bit 1326. The drilling fluid can flow out from the drill bit 1326 and be returned to the surface 1304 through an annular area 1340 between the drill pipe 1318 and the sides of the borehole 1312. The drilling fluid may then be returned to the mud pit 1334, where such fluid is filtered. In some embodiments, the drilling fluid can be used to cool the drill bit 1326, as well as to provide lubrication for the drill bit 1326 during drilling operations. Additionally, the drilling fluid may be used to remove subsurface formation 1314 cuttings created by operating the drill bit 1326.

In various embodiments, the tool 1305 may be included in a tool body 1370 coupled to a logging cable 1374 such as, for example, for wireline applications. The tool body 1370 containing the tool 1305 can include electronics to activate one or more transmitters of the tool 1305 and collect responses from one or more receivers of the tool 1305. Such electronics can include a processing unit to conduct nuclear magnetic resonance inversion and provide results to the surface over a standard communication mechanism for operating a well. Alternatively, electronics can include a communications interface to provide signals output by receivers of the tool 1305 to the surface over a standard communication mechanism for operating a well, where these output signals can be analyzed at a processing unit at the surface to conduct nuclear magnetic resonance inversion. The logging cable 1374 may be realized as a wireline (multiple power and communication lines), a mono-cable (a single conductor), and/or a slick-line (no conductors for power or communications), or other appropriate structure for use in the bore hole 1312.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. A method comprising:
generating a tipping pulse from a downhole nuclear magnetic resonance (NMR) tool into a subsurface formation to start a first transverse relaxation time (T2) echo train pulse sequence, wherein the NMR tool has a first arrangement of magnets and a second arrangement of magnets positioned longitudinally along the NMR tool, wherein a plurality of transmitters and a plurality of receivers are affixed to the tool structure in between the first and second arrangement of magnets, wherein the combination of transmitters and receivers is communicably coupled to a control unit that manages generation and collection of pulses from the combination of transmitters and receivers;
generating a number of refocusing pulses following the tipping pulse as part of the first T2 echo train pulse sequence, the first T2 echo train pulse sequence having an end refocusing pulse;
generating a recovery pulse after generating the end refocusing pulse so as to reduce a recovery time needed for magnetization to achieve a level of repolarization after the first T2 echo train pulse sequence; and
when the level of repolarization is achieved following the recovery pulse of the first T2 echo train pulse sequence, generating another tipping pulse from the downhole NMR tool into the subsurface formation to start a second T2 echo train pulse sequence.

2. The method of claim 1, wherein the tipping pulse is a 90° pulse, each refocusing pulse is a 180° pulse, and the recovery pulse is a 90° pulse.

3. The method of claim 1 or 2, wherein the recovery pulse is applied at a center of an echo following the end refocusing pulse.

4. The method of claim 1 or 2, wherein the level of repolarization is assigned as a percentage of full repolarization.

5. The method of claim 4, wherein the percentage is ninety-seven percent.

6. The method of claim 1 or 2, wherein the recovery time is based on the number of refocusing pulses and the level of repolarization.

7. The method of claim 6, wherein the number of refocusing pulses is based on a selected wait time.

8. The method of claim 6, wherein the number of refocusing pulses is less than a number of refocusing pulses corresponding to a wait time of 5 seconds.

9. The method of claim 1 or 2, wherein the second T2 echo train pulse sequence is generated at a frequency different from that of the first T2 echo train pulse sequence.

10. A machine-readable storage device having instructions stored thereon, which, when performed by a machine, cause the machine to perform operations to:
generate a tipping pulse from a downhole nuclear magnetic resonance (NMR) tool into a subsurface formation to start a first transverse relaxation time (T2) echo train pulse sequence, wherein the NMR tool has a first arrangement of magnets and a second arrangement of magnets positioned longitudinally along the NMR tool, wherein a plurality of transmitters and a plurality of receivers are affixed to the tool structure in between the first and second arrangement of magnets, wherein the combination of transmitters and receivers is communicably coupled to a control unit that manages generation and collection of pulses from the combination of transmitters and receivers;
generate a number of refocusing pulses following the tipping pulse as part of the first T2 echo train pulse sequence, the first T2 echo train pulse sequence having an end refocusing pulse;
generate a recovery pulse after generating the end refocusing pulse so as to reduce a recovery time needed for magnetization to achieve a level of repolarization after the first T2 echo train pulse sequence; and
when the level of repolarization is achieved following the recovery pulse of the first T2 echo train pulse sequence, generating another tipping pulse from the downhole NMR tool into the subsurface formation to start a second T2 echo train pulse sequence.

11. The machine-readable storage device of claim 10, wherein the tipping pulse is a 90° pulse, each refocusing pulse is a 180° pulse, and the recovery pulse is a 90° pulse.

12. The machine-readable storage device of claim 10 or 11, wherein the recovery pulse is applied at a center of an echo following the end refocusing pulse.

13. The machine-readable storage device of claim 10 or 11, wherein the level of repolarization is assigned as a percentage of full repolarization.

14. The machine-readable storage device of claim 13, wherein the percentage is ninety-seven percent.

15. The machine-readable storage device of claim 10 or 11, wherein the recovery time is based on the number of refocusing pulses and the level of repolarization.

16. The machine-readable storage device of claim 15, wherein the number of refocusing pulses is based on a selected wait time.

17. The machine-readable storage device of claim 16, wherein the number of refocusing pulses is less than a number of refocusing pulses corresponding to a wait time of 5 seconds.

18. The machine-readable storage device of claim 10 or 11, wherein the second T2 echo train pulse sequence is generated at a frequency different from that of the first T2 echo train pulse sequence.

19. A system comprising:
a downhole nuclear magnetic resonance (NMR) tool; and
a control unit coupled to the downhole nuclear magnetic resonance tool to control the downhole nuclear magnetic resonance tool to perform operations to:
generate a tipping pulse from the downhole nuclear magnetic resonance tool into a subsurface formation to start a first transverse relaxation time (T2) echo train pulse sequence;
generate a number of refocusing pulses following the tipping pulse as part of the first T2 echo train pulse sequence, the first T2 echo train pulse sequence having an end refocusing pulse;
generate a recovery pulse after generating the end refocusing pulse so as to reduce a recovery time needed for magnetization to achieve a level of repolarization-after the first T2 echo train pulse sequence; and
when the level of repolarization is achieved following the recovery pulse of the first T2 echo train pulse sequence, generating another tipping pulse from the downhole NMR tool into the subsurface formation to start a second T2 echo train pulse sequence,
wherein the NMR tool has a first arrangement of magnets and a second arrangement of magnets positioned longitudinally along the NMR tool, wherein a plurality of transmitters and a plurality of receivers are affixed to the tool structure in between the first and second arrangement of magnets, wherein the combination of transmitters and receivers is communicably coupled to a control unit that manages generation and collection of pulses from the combination of transmitters and receivers.

20. The system of claim 19, wherein the tipping pulse is a 90° pulse, each refocusing pulse is a 180° pulse, and the recovery pulse is a 90° pulse.

21. The system of claim 19 or 20, wherein the recovery pulse is applied at a center of an echo following the end refocusing pulse.

22. The system of claim 19 or 20, wherein the level of repolarization is assigned as a percentage of full repolarization.

23. The system of claim 19 or 20, wherein the percentage is ninety-seven percent.

24. The system of claim 19 or 20, wherein based on the number of refocusing pulses and the level of repolarization.

25. The system of claim 24, wherein the number of refocusing pulses is based on a selected wait time.

26. The system of claim 25, wherein the number of refocusing pulses is less than a number of refocusing pulses corresponding to a wait time of 5 seconds.

27. The system of claim 19 or 20, wherein the second T2 echo train pulse sequence is generated at a frequency different from that of the first T2 echo train pulse-sequence.

* * * * *